(12) United States Patent
Stadler et al.

(10) Patent No.: US 7,344,730 B1
(45) Date of Patent: Mar. 18, 2008

(54) SOIL GRANULATES WITH CONTROLLED ACTIVE INGREDIENT RELEASE (CR SOIL GRANULATES)

(75) Inventors: Reinhold Stadler, Kirrweiler (DE); Reiner Kober, Fußgönheim (DE); Karl-Heinrich Schneider, Kleinkarlbach (DE); Reinhold Saur, Böhl-Iggelheim (DE); Herbert Bayer, Mannheim (DE); Karl Kolter, Limburgerhof (DE); Michael Seufert, Bad Dürkheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 09/762,044

(22) PCT Filed: Jul. 28, 1999

(86) PCT No.: PCT/EP99/05407

§ 371 (c)(1),
(2), (4) Date: Feb. 1, 2001

(87) PCT Pub. No.: WO00/07443

PCT Pub. Date: Feb. 17, 2000

(30) Foreign Application Priority Data

Aug. 5, 1998  (DE) .................................. 198 35 218
Oct. 13, 1998  (DE) .................................. 198 46 893

(51) Int. Cl.
*A01N 37/52* (2006.01)

(52) U.S. Cl. ...................... 424/419; 424/420; 424/421; 514/162; 514/241; 514/508

(58) Field of Classification Search ................ 424/405, 424/408–409, 417–421; 514/506–508
See application file for complete search history.

(56) References Cited

U.S. PATENT DOCUMENTS 4,663,359 A * 5/1987 Rei .............................. 521/85
4,756,844 A    7/1988 Walles

FOREIGN PATENT DOCUMENTS

| CA | 2178655 | 6/1995 |
| CA | 2 228 818 | 9/1998 |
| EP | 380 836 | 8/1990 |
| EP | 0582561 | * 2/1994 |
| EP | 868 912 | 10/1998 |
| WO | 92/17424 | 10/1992 |
| WO | 95/16350 | 6/1995 |
| WO | 98/14413 | 4/1998 |

* cited by examiner

*Primary Examiner*—Neil S. Levy
(74) *Attorney, Agent, or Firm*—Novak Druce + Quigg LLP

(57) ABSTRACT

The present invention relates to soil-applied CR granules obtainable by applying an active-ingredient-comprising coating to a solid carrier in a fluidized bed, to a process for the preparation of these soil-applied granules, and to a method for controlling phytopathogenic fungi, undesired vegetation, undesired attack by insects and/or for regulating the growth of plants using the soil-applied CR granules according to the invention.

11 Claims, No Drawings

SOIL GRANULATES WITH CONTROLLED ACTIVE INGREDIENT RELEASE (CR SOIL GRANULATES)

The present invention relates to soil-applied CR granules which can be obtained by applying an active-ingredient-comprising coating to a solid carrier in a fluidized bed with a defined heat input adjustable to 6000 to 25,000 KJ/Kg [sic] of coating polymer, to soil-applied CR granules with an active-ingredient-comprising coating of 0.1-25% by weight of one or more active ingredients, 1-40% by weight of one or more coating polymers and 0-60% by weight of one or more additives, to a process for the preparation of these soil-applied granules, and to a method for controlling phytopathogenic fungi, undesired vegetation, undesired attack by insects and/or for regulating the growth of plants using the soil-applied CR granules according to the invention.

It is generally known to use coating polymers for fixing crop protection active ingredients on a solid carrier in such a manner that the active ingredient is only gradually released and can thus develop its action over a prolonged period ("slow-release formulation"). WO-A 92 17424 describes fertilizer granules which are coated with an ionically and covalently crosslinked copolymer of ethylene and the zinc salt of methacrylic acid. EP-A 0 380 836 discloses the non-covalently crosslinked, partially neutralized equivalents to the copolymers described in WO-A-9217424 as suitable for coating agrochemicals which are to be released slowly and in a controlled fashion. A process for coating small particles which comprise an active ingredient, which may be a crop protection agent, is described in U.S. Pat. No. 4,756,844. However, the disadvantage of the current products is that they still tend to agglomerate greatly, which means that the flowability of the formulated product is lost and that the release rate of the active ingredient cannot be adjusted by means of process control.

It is an object of the present invention to find a formulation for crop protection active ingredients which does not exhibit these disadvantageous characteristics.

It is a further object of the present invention to develop slow-release formulations which allow the use of phytotoxic active ingredients for treating plant diseases.

It is a further object of the present invention to develop novel coating techniques using specific and novel coating polymers which provide the encapsulated active ingredient in a tailored manner, with a controlled release rate, systemically and transapically over a substantial vegetation period of the plant in the form of granules for co-drilling.

We have found that this object is achieved by soil-applied CR granules as claimed in claim 1.

There has furthermore been found a process for their preparation and the use of those compositions which comprise fungicidal crop protection active ingredient for controlling harmful fungi.

The construction of semipermeable monolayer or polylayer coatings on the soil-applied CR granules and exact metering of the heat input supplied into a fluidized-bed apparatus allows the active ingredient to be available for up to a period of over 9 months.

Preferred soil-applied CR granules according to the invention are intended to offer complete protection against fungal pathogens, to be nonphytotoxic and, finally, to replace fungicide spray treatments when they are applied by co-drilling together with the seed of the annual or perennial plant.

Suitable crop protection active ingredients are herbicidal, growth-regulatory, insecticidal and, in particular, fungicidal active ingredients.

Suitable systemic active ingredients which are available belong to the fungicidal substance classes of the azoles, morpholines, valinamides, strobilurins and salicylates as distant derivatives of active ingredients of the Bion® type. Surprisingly, selected experiments in which application was effected in the form of the soil-applied CR granules according to the invention led to similarly successful biological results as when two spray treatments with commercially available fungicides were carried out; in some cases, the biological results were even better.

Thus, surprisingly, when using acetylsalicylic acid as active ingredient component, activity-enhancing effects were observed upon soil application and combination with strobilurins.

The following list of herbicides identifies examples of active ingredients which are possible:

b1 1,3,4-Thiadiazoles:
  buthidazole, cyprazole b2 Amides:
  allidochlor (CDAA), benzoylprop-ethyl, bromobutide, chlorthiamid, dimepiperate, dimethenamid, s-dimethenamid, diphenamid, etobenzanid (benzchlomet), flamprop-methyl, fluthiamide, fosamin, isoxaben, monalide, naptalame, pronamid (propyzamid), propanil b3 Aminophosphoric acids:
  bilanafos, (bialaphos), buminafos, glufosinate-ammonium, glyphosate, sulfosate b4 Aminotriazoles:
  amitrol b5 Anilides:
  anilofos, mefenacet b6 Aryloxyalkanoic acids:
  2,4-D, 2,4-DB, clomeprop, dichlorprop, dichlorprop-p, dichlorprop-p (2,4-DP-P), fenoprop (2,4,5-TP), fluoroxypyr, MCPA, MCPB, mecoprop, mecoprop-P, napropamide, napropanilide, triclopyr b7 Benzoic acids:
  chloramben, dicamba b8 Benzothiadiazinones:
  bentazone b9 Bleachers:
  clomazone (dimethazone), diflufenican, fluorochloridone, flupoxam, fluridone, pyrazolate, sulcotrione (chlormesulone), isoxaflutole, isoxachlortole, mesotrione b10 Carbamates:
  asulam, barban, butylate, carbetamid, chlorbufam, chlorpropham, cycloate, desmedipham, di-allate, EPTC, esprocarb, molinate, orbencarb, pebulate, phenisopham, phenmedipham, propham, prosulfocarb, pyributicarb, sulf-allate (CDEC), terbucarb, thiobencarb (benthiocarb), tiocarbazil, tri-allate, vernolate b11 Quinoline [sic] acids:
  quinclorac, quinmerac b12 Chloracetanilides:
  acetochlor, alachlor, butachlor, butenachlor, diethatyl [sic] ethyl, dimethachlor, metazachlor, metolachlor, pretilachlor, propachlor, prynachlor, terbuchlor, thenylchlor, xylachlor, s-metolachlor b13 Cyclohexenones:
   alloxydim, tepraloxydim, clethodim, cloproxydim, cycloxydim, sethoxydim, tralkoxydim, 2-{1-[2-(4-chlorophenoxy)propyloxyimino]butyl}-3-hydroxy-5-(2H-tetrahydrothiopyran-3-yl)-2-cyclohexen-1-one, butroxydim, clefoxydim b14 Dichloropropionic acids:
   dalapon b15 Dihydrobenzofurans:
   ethofumesate b16 Dihydrofuran-3-ones:
   flurtamone b17 Dinitroanilines:
   benefin, butralin, dinitramin, ethalfluralin, fluchloralin, isopropalin, nitralin, oryzalin, pendimethalin, prodiamine, profluralin, trifluralin b18 Dinitrophenols:
   bromofenoxim, dinoseb, dinoseb-acetate, dinoterb, DNOC b19 Diphenyl ethers:
   acifluorfen-sodium, aclonifen, bifenox, chlornitrofen (CNP), difenoxuron, ethoxyfen, fluorodifen, fluoroglycofen-ethyl, fomesafen, furyloxyfen, lactofen, nitrofen, nitrofluorfen, oxyfluorfen b20 Dipyridylenes:
   cyperquat, difenzoquat-methylsulfate, diquat, paraquat dichloride b21 Ureas:
   benzthiazuron, buturon, chlorbromuron, chloroxuron, chlortoluron, cumyluron, dibenzyluron, cycluron, dimefuron, diuron, dymron, ethidimuron, fenuron, fluormeturon, isoproturon, isouron, karbutilat, linuron, methabenzthiazuron, metobenzuron, metoxuron, monolinuron, monuron, neburon, siduron, tebuthiuron, trimeturon b22 Imidazoles:
   isocarbamid b23 Imidazolinones:
   imazamethapyr, imazapyr, imazaquin, imazethabenz-methyl (imazame), imazethapyr, imazapic b24 Oxadiazoles:
   methazole, oxadiargyl, oxadiazon b25 Oxiranes:
   tridiphane b26 Phenols:
   bromoxynil, ioxynil b27 Phenoxyphenoxypropionic esters:
   clodinafop, cloquintocet, cyhalofop-butyl, diclofop-methyl, fenoxaprop-ethyl, fenoxaprop-p-ethyl, fenthiapropethyl, fluazifop-butyl, fluazifop-p-butyl, haloxyfop-ethoxyethyl, haloxyfop-methyl, haloxyfop-p-methyl, isoxapyrifop, propaquizafop, quizalofop-ethyl, quizalofop-p-ethyl, quizalofop-tefuryl b28 Phenylacetic acids:
   chlorfenac (fenac)

b29 Phenylpropionic acids:
   chlorophenprop-methyl [sic]

b30 Protoporphyrinogen IX oxydase inhibitors:
   benzofenap, cinidon-ethyl, flumiclorac-pentyl, flumioxazin, flumipropyn, flupropacil, fluthiacet-methyl, pyrazoxyfen, sulfentrazone, thidiazimin, carfentrazone b31 Pyrazoles
   nipyraclofen, pyraflufen-ethyl b32 Pyridazines:
   chloridazon, maleic hydrazide, norflurazon, pyridate b33 Pyridinecarboxylic acids:
   clopyralid, dithiopyr, picloram, thiazopyr, diflufenzopyr b34 Pyrimidyl ethers:
   pyrithiobac-acid, pyrithiobac-sodium, KIH-2023, KIH-6127, pyribenzoxym b35 Sulfonamides:
   flumetsulam, metosulam b36 Sulfonylureas:
   amidosulfuron, azimsulfuron, bensulfuron-methyl, chlorimuron-ethyl, chlorsulfuron, cinosulfuron, cyclosulfamuron, ethametsulfuron methyl, ethoxysulfuron, flazasulfuron, halosulfuron-methyl, imazosulfuron, metsulfuron-methyl, nicosulfuron, primisulfuron, prosulfuron, pyrazosulfuron-ethyl, rimsulfuron, sulfometuron-methyl, thifensulfuron-methyl, triasulfuron, tribenuron-methyl, triflusulfuron-methyl, N-[[[4-methoxy-6-(trifluoromethyl)-1,3,5-triazin-2-yl]amino]-carbonyl]-2-(trifluoromethyl)benzenesulfonamide, sulfosulfuron, idosulfuron b37 Triazines:
   ametryn, atrazine, aziprotryn, cyanazine, cyprazine, desmetryn, dimethamethryn, dipropetryn, eglinazine-ethyl, hexazinone, procyazine, prometon, prometryn, propazine, secbumeton, simazine, simetryn, terbumeton, terbutryn, terbutylazine [sic], trietazine b38 Triazinones:
   ethiozin, metamitron, metribuzin b39 Triazolecarboxamides:
   triazofenamid b40 Uracils:
   bromacil, lenacil, terbacil b41 Various:
   benazolin, benfuresate, bensulide, benzofluor, butamifos, cafenstrole, chlorthal-dimethyl (DCPA), cinmethylin, dichlobenil, endothall, fluorbentranil, mefluidide, perfluidone, piperophos, flucabazone, oxaciclomefone (MY 100)

The following list of compounds with growth-regulatory activity shows examples of active ingredients which are possible from amongst this group:

1-naphthylacetamide, 1-naphthylacetic acid, 2-naphthyloxyacetic acid, 3-CPA, 4-CPA, ancymidol, anthraquinone, BAP, butifos; tribufos, butralin, chlorflurenol, chlormequat, clofencet, cyclanilide, daminozide, dicamba, dikegulac-sodium, dimethipin, chlorfenethol, etacelasil, ethephon, ethychlozate, fenoprop, 2,4,5-TP, fluoridamid, flurprimidol, flutriafol, gibberellic acid, gibberillin, guazatine, imazalil, indolylbutyric acid, indolylacetic acid, karetazan, kinetin, lactidichlor-ethyl, maleic hydrazide, mefluidide, mepiquat-chloride, naptalam, paclobutrazole, prohexadione calcium, quinmerac, sintofen, tetcyclacis, thidiazuron, triiodobezoic [sic] acid, triapenthenol, triazethan, tribufos, trinexapac-ethyl, uniconazole.

The list of insecticides which follows indicates examples of active ingredients which are possible:

Neonicotinoids/chloronicotinyl compounds:

imidacloprid, acetamiprid, nitenpyram, thiacloprid, thiamethoxam, tefuranitdine, organophosphates, acephate, azinphos-methyl, chlorpyrifos, dimethoate, disulfoton, fosthiazate, methamidophos, methidathion, methylparathion, oxydemeton-methyl, phorate, phosalone, phosmet, profenofos, trichlorfon carbamates such as alanycarb, aldicarb, benfuracarb, carbofuran, carbosulfan, furathiocarb, methomyl, oxamyl, pirimicarb, thiodicarb pyrethroids such as bifenthrin, cyfluthrin, cypermethrin, deltamethrin, esfenvalerate, fenpropathrin, lambda-cyhalothrin, permethrin, tau-fluvalinate, tralomethrin, zeta-cypermethrin urea derivatives such as diflubenzuron, flucycloxuron, flufenoxuron, hexaflumuron, lufenuron, novaluron, triflumuron juvenoids such as buprofezin, diofenolan, fenoxycarb, pyriproxifen, methoxyfenozide, tebufenozide various such as abamectin, spinosad, amitraz, cartap, chlorfenapyr, diafenthiuron, fipronil pyridaben, tebufenpyrad, fenazaquin, fenpyroxymate, thiocyclam, silafluofen The list of fungicides which follows shows examples of active ingredients which are possible:

sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides [sic], ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropyl carbonate, diisopropyl 5-nitroisophthalate;

heterocyclic substances, such as 2-heptadecyl-2-imidazoline acetate, 2,4-dichloro-6-(o-chloroanilino)-s-triazine, 0,0-diethyl phthalimidophosphonothioate, 5-amino-1-[bis(dimethylamino)-phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl)benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thio[sic]1-oxide, 8-hydroxyquinoline and its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis-1-(2,2,2-trichloroethyl)formamide, 1-(3,4-dichloroanilino)-1-formylamino-2,2,2-trichloroethane, 2,6-dimethyl-N-tridecylmorpholine and its salts, 2,6-dimethyl-N-cyclododecylmorpholine and its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N,N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-yl-methyl]-1H-1,2,4-triazole, a-(2-chlorophenyl)-a-(4-chlorophenyl)-5-pyrimidinemethanol[sic], 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, anilinopyrimidines such as N-(4,6-dimethylpyrimidin-2-yl)aniline, N-[4-methyl-6-(1-propynyl)pyrimidin-2-yl]aniline, N-(4-methyl-6-cyclopropylpyrimidin-2-yl)aniline, phenylpyrroles such as 4-(2,2-difluoro-1,3-benzodioxol-4-yl)pyrrole-3-carbonitrile, cinnamamides such as 3-(4-chlorophenyl)-3-(3,4-dimethoxyphenyl)acryloylmorpholine, and a variety of fungicides, such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl(-5-methyl-5-methoxymethyl]-1,3-oxazolidine-2,4-dione[sic], 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-a-(1H-1,2,4-triazolyl-1-methyl)benzhydryl[sic]alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole, 2-(4-chlorophenyl)-3-cyclopropyl-1-(1H-1,2,4-triazol-1-yl)butan-2-ol, 3-chloro-4-[4-methyl-2-(1H-1,2,4-triazol-1-ylmethyl)-1,3-dioxo-lan-2-yl]phenyl 4-chlorophenyl ether, 1,3-dimethyl-5-chloro-1,3-dimethyl[2,3-(2,4,4-trimethyltetrahydrofuran)pyrazol-4-carboxanilide], 2',6'-dibromo-2-methyl-4'-trofluoromethoxy-4-trifluoromethylthia-zole-5-carboxanilide[sic], [2-(4'- chlorophenyl)-2-chloronicotinanilide[sic], N—[(R)-1-(2,4-dichlorophenyl)ethyl]-(S)-2-cyano-3,3-dimethylbutanamide, N—[(R)-1-(4-chlorophenyl)ethyl]-(S)-2,2-cyclopropyl-2',2-dichloro-3'-methylbutanamide, 3-allyloxy-1,2-benzisothiazole 1,1-dioxide, 2,3-benzisothiadiazole-1-carboxylic acid thiol ester, 1,2,5,6-tetrahydropyrrolo[3,2,1-i,j]quinolin-4-one, 5-methyl-1,2,4-triazolo[3,4-b]benzothiazole, di-idopropyl[sic]1,3-dithiolan-2-ylidenemalonate, 4-(2,2-difluoro-1,3-benzodioxol-4-yl)pyrrole-3-carbonitrile, N-(i-propoxycarbonyl)-L-valine-(R)-1-(2-naphthyl)ethylamide, N-(i-propoxycarbonyl)-L-valine-(R—(R,S)-1-(4-methylphenyl)ethylamide, strobilurins such as methyl E-methoximino[α-(o-tolyloxy)-o-tolyl]acetate, methyl E-2-{2-[6-(2-cyanophenoxy)pyrimidin-4-yloxy]phenyl}-3-methoxyacrylate, N-methyl E-methoximino[a-(2-phenoxyphenyl)]acetamide, N-methyl E-methoximino[a-(2,5-dimethylphenoxy)-o-tolyl]-acetamide.

From amongst the class of the strobilurins, the following fungicidally active compounds of the formula I may preferably be mentioned:

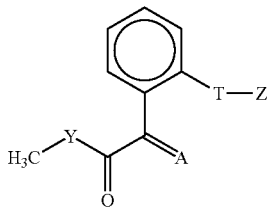

in which the substituents have the following meanings:
A is NOCH$_3$, CHOCH$_3$, CHCH$_3$;
Y is O, NH;
T is oxygen or oxymethylene;
Z is a group X, N=C(R$^1$)W or N=C(R$^1$)—C(R$^2$)=NOR$^3$;
X is unsubstituted or substituted heterocyclyl, unsubstituted or substituted aryl, unsubstituted or substituted hetaryl;
W is unsubstituted or substituted alkyl, unsubstituted or substituted alkenyl, unsubstituted or substituted alkynyl, unsubstituted or substituted cycloalkyl, unsubstituted or substituted cycloalkenyl, unsubstituted or substituted heterocyclyl, unsubstituted or substituted aryl or unsubstituted or substituted hetaryl;
R$^1$ is hydrogen, cyano, C$_1$-C$_4$-alkyl, C$_1$-C$_4$-haloalkyl, C$_1$-C$_4$-alkoxy, C$_1$-C$_4$-alkoxy-C$_1$-C$_4$-alkyl, C$_3$-C$_6$-cycloalkyl;
R$^2$ is hydrogen, cyano, halogen, C(R$^d$)=NOR$^3$ or W, OW, SW or NR$^c$W, where
R$^c$ is hydrogen, alkyl, alkenyl or alkynyl;
R$^d$ is hydrogen or alkyl;
R$^3$ is hydrogen, unsubstituted or substituted alkyl, unsubstituted or substituted alkenyl or unsubstituted or substituted alkynyl
where
X is heterocyclyl which may be fully or partially halogenated and/or may carry 1 to 3 of the following radicals:
cyano, C$_1$-C$_4$-alkyl, C$_1$-C$_4$-haloalkyl or C$_1$-C$_4$-alkoxy;
aryl, hetaryl, where the cyclic radicals may be partially or fully halogenated and/or may carry one to three of the following groups:
cyano, nitro, hydroxyl, mercapto, amino, carboxyl, aminocarbonyl, aminothiocarbonyl, C$_1$-C$_6$-alkyl, C$_1$-C$_6$-haloalkyl, C$_1$-C$_6$-alkylcarbonyl, C$_1$-C$_6$-alkylsulfonyl, C$_1$-C$_6$-alkylsulfoxyl, C$_3$-C$_6$-cycloalkyl, C$_1$-C$_6$-alkoxy, C$_1$-C$_6$-haloalkoxy, C$_1$-C$_6$-alkoxycarbonyl, C$_1$-C$_6$-alkylthio, C$_1$-C$_6$-alkylamino, di-C$_1$-C$_6$-alkylamino, C$_1$-C$_6$-alkylaminocarbonyl, di-C$_1$-C$_6$-alkylaminocarbonyl, C$_1$-C$_6$-alkylaminothiocarbonyl, di-C$_1$-C$_6$-alkylaminothiocarbonyl, C$_2$-C$_6$-alkenyl, C$_2$-C$_6$-alkenyloxy, benzyl, benzyloxy, aryl, aryloxy, arylthio, heteroaryl, heteroaryloxy, heteroarylthio, C$_3$-C$_6$-alkynyloxy, C$_1$-C$_4$-alkylenedioxy, which may be halogenated, or C(=NOR$^d$)-Γ$_l$-R$^{d'}$ where
R$^d$ is hydrogen or C$_1$-C$_6$-alkyl;
Γ is oxygen, sulfur or NR$^d$;
l is 0 or 1 and
the cyclic groups for their part may be partially or fully halogenated and/or may carry 1 to 3 of the following substituents: cyano, nitro, hydroxyl, C$_1$-C$_6$-alkyl, C$_1$-C$_6$-haloalkyl, C$_1$-C$_6$-alkylcarbonyl, C$_3$-C$_6$-cycloalkyl, C$_1$-C$_6$-alkoxy, C$_1$-C$_6$-haloalkoxy, C$_1$-C$_6$-alkoxycarbonyl, C$_1$-C$_6$-alkylthio, C$_1$-C$_6$-alkylamino, di-C$_1$-C$_6$-alkylamino, C$_2$-C$_6$-alkenyl, C$_2$-C$_6$-alkenyloxy, C$_3$-C$_6$-alkynyloxy and C$_1$-C$_4$-alkylenedioxy which may be halogenated,
W is C$_1$-C$_6$-alkyl, C$_2$-C$_6$-alkenyl or C$_2$-C$_6$-alkynyl, where these groups may be fully or partially halogenated and/or may carry 1 to 3 of the following radicals:
cyano, C$_1$-C$_6$-alkoxy, C$_1$-C$_6$-haloalkoxy, C$_1$-C$_6$-alkoxycarbonyl, C$_3$-C$_6$-cycloalkyl, heterocyclyl, aryl or hetaryl, where
the cyclic groups for their part may be partially or fully halogenated and/or may carry 1 to 3 of the following radicals:
cyano, nitro, C$_1$-C$_4$-alkyl, C$_1$-C$_4$-haloalkyl, C$_1$-C$_4$-alkoxy, C$_1$-C$_4$-haloalkoxy; or
is C$_3$-C$_6$-cycloalkyl, C$_3$-C$_6$-cycloalkenyl or heterocyclyl, where these groups may be fully or partially halogenated and/or may carry 1 to 3 of the following radicals:
cyano, C$_1$-C$_4$-alkyl, C$_1$-C$_4$-haloalkyl or C$_1$-C$_4$-alkoxy; or
is aryl or heteroaryl,
where these radicals may be partially or fully halogenated and/or may carry one to three of the following groups:
cyano, nitro, hydroxyl, mercapto, amino, carboxyl, aminocarbonyl, aminothiocarbonyl, C$_1$-C$_6$-alkyl, C$_1$-C$_6$-haloalkyl, C$_1$-C$_6$-alkylcarbonyl, C$_1$-C$_6$-alkylsulfonyl, C$_1$-C$_6$-alkylsulfoxyl, C$_3$-C$_6$-cycloalkyl, C$_1$-C$_6$-alkoxy, C$_1$-C$_6$-haloalkoxy, C$_1$-C$_6$-alkoxycarbonyl, C$_1$-C$_6$-alkylthio, C$_1$-C$_6$-alkylamino, di-C$_1$-C$_6$-alkylamino, C$_1$-C$_6$-alkylaminocarbonyl, di-C$_1$-C$_6$-alkylaminocarbonyl, C$_1$-C$_6$-alkylaminothiocarbonyl, di-C$_1$-C$_6$-alkylaminothiocarbonyl, C$_2$-C$_6$-alkenyl, C$_2$-C$_6$-alkenyloxy, benzyl, benzyloxy, aryl, aryloxy, arylthio, heteroaryl, heteroaryloxy, heteroarylthio, C$_3$-C$_6$-alkynyloxy, C$_1$-C$_4$-alkylenedioxy, which may be halogenated, or C(=NOR$^d$)-Γ$_l$-R$^{d'}$ where
R$^d$ is hydrogen or C$_1$-C$_6$-alkyl;
Γ is oxygen, sulfur or NR$^d$;
l is 0 or 1 and
the cyclic groups for their part may be partially or fully halogenated and/or may carry 1 to 3 of the following substituents:
cyano, nitro, hydroxyl, C$_1$-C$_6$-alkyl, C$_1$-C$_6$-haloalkyl, C$_1$-C$_6$-alkylcarbonyl, C$_3$-C$_6$-cycloalkyl, C$_1$-C$_6$-alkoxy, C$_1$-C$_6$-haloalkoxy, C$_1$-C$_6$-alkoxycarbonyl, C$_1$-C$_6$-alkylthio, C$_1$-C$_6$-alkylamino, di-C$_1$-C$_6$-alkylamino, C$_2$-C$_6$-alkenyl, C$_2$-C$_6$-alkenyloxy, C$_3$-C$_6$-alkynyloxy and C$_1$-C$_4$-alkylenedioxy which may be halogenated, $R^2$ is hydrogen, cyano, halogen, $C(R^d)$=$NOR^3$ or W, OW, SW or $NR^cW$, where $R^c$ is hydrogen, $C_1$-$C_6$-alkyl, $C_2$-$C_6$-alkenyl or $C_2$-$C_6$-alkynyl;

$R^d$ is hydrogen or $C_1$-$C_4$-alkyl; and $R^3$ is hydrogen, $C_1$-$C_6$-alkyl, $C_1$-$C_6$-cyanoalkyl, $C_2$-$C_6$-alkenyl, $C_2$-$C_6$-alkynyl, $C_1$-$C_4$-alkoxy-$C_1$-$C_6$-alkyl or $C_3$-$C_6$-cycloalkyl-$C_1$-$C_4$-alkyl, where these groups may be partially or fully halogenated and the cycloalkyl groups may additionally carry 1 to 3 $C_1$-$C_4$-alkyl radicals;

and their salts.

Collective terms represent the following substituents:

Halogen: fluorine, chlorine, bromine and iodine;

Alkyl: saturated, straight-chain or branched hydrocarbon radicals having 1 to 4, 6 or 10 carbon atoms, for example $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Haloalkyl: straight-chain or branched alkyl groups having 1 to 10 carbon atoms (as mentioned above), where the hydrogen atoms in these groups may be partially or fully replaced by halogen atoms as mentioned above, for example $C_1$-$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 10 carbon atoms (as mentioned above) which are attached to the skeleton via an oxygen atom (—O—);

Haloalkoxy: straight-chain or branched haloalkyl groups having 1 to 10 carbon atoms (as mentioned above) which are attached to the skeleton via an oxygen atom (—O—);

Alkylthio: straight-chain or branched alkyl groups having 1 to 10 or 1 to 4 carbon atoms (as mentioned above) which are attached to the skeleton via a sulfur atom (—S—);

Alkylamino: a straight-chain or branched alkyl group having 1 to 10 carbon atoms (as mentioned above) which is attached to the skeleton via an amino group (—NH—);

Dialkylamino: two independent straight-chain or branched alkyl groups having in each case 1 to 10 carbon atoms (as mentioned above) which are attached to the skeleton via a nitrogen atom;

Alkylcarbonyl: a straight-chain or branched alkyl group having 1 to 10 carbon atoms (as mentioned above) which is attached to the skeleton via a carbonyl group (—CO—);

Alkoxycarbonyl: an alkoxy group having 1 to 10 carbon atoms (as mentioned above) which is attached to the skeleton via a carbonyl group (—CO—);

Alkylthiocarbonyl: an alkylthio group having 1 to 10 carbon atoms (as mentioned above) which is attached to the skeleton via a carbonyl group (—CO—);

Alkylaminocarbonyl: an alkylamino group having 1 to 10 carbon atoms (as mentioned above) which is attached to the skeleton via a carbonyl group (—CO—);

Dialkylaminocarbonyl: a dialkylamino group (as mentioned above) which is attached to the skeleton via a carbonyl group (—CO—);

Alkylcarbonyloxy: a straight-chain or branched alkyl group having 1 to 10 carbon atoms (as mentioned above) which is attached to the skeleton via a carbonyloxy group (—$CO_2$—);

Alkylsulfonyl: a straight-chain or branched alkyl group having 1 to 10 carbon atoms (as mentioned above) which is attached to the skeleton via a sulfonyl group (—$SO_2$—);

Alkoxysulfonyl: an alkoxy group having 1 to 10 carbon atoms (as mentioned above) which is attached to the skeleton via a sulfonyl group (—$SO_2$—);

Alkenyl: unsaturated, straight-chain or branched hydrocarbon radicals having 2 to 4, 6, 8 or 10 carbon atoms and a double bond in any position, for example $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3 pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Haloalkenyl: unsaturated, straight-chain or branched hydrocarbon radicals having 2 to 10 carbon atoms and a double bond in any position (as mentioned above), where the hydrogen atoms in these groups may be partly or fully replaced by halogen atoms as mentioned above, in particular by fluorine, chlorine and bromine;

Alkenyloxy: unsaturated, straight-chain or branched hydrocarbon radicals having 3 to 10 carbon atoms and a double bond in any position which is not adjacent to the hetero atom (as mentioned above), which are attached to the skeleton via an oxygen atom (—O—);

Haloalkenyloxy: unsaturated, straight-chain or branched alkenyloxy groups having 3 to 10 carbon atoms (as mentioned above), where the hydrogen atoms in these groups may be partly or fully replaced by halogen atoms, in particular by fluorine, chlorine and bromine;

Alkenylthio: unsaturated, straight-chain or branched hydrocarbon radicals having 3 to 10 carbon atoms and a double bond in any position which is not adjacent to the hetero atom (as mentioned above), which are attached to the skeleton via a sulfur atom (—S—);

Alkenylamino: unsaturated, straight-chain or branched hydrocarbon radicals having 3 to 10 carbon atoms and a double bond in any position which is not adjacent to the hetero atom (as mentioned above), which are attached to the skeleton via an amino group (—NH—);

Alkenylcarbonyl: unsaturated, straight-chain or branched hydrocarbon radicals having 2 to 10 carbon atoms and a double bond in any position (as mentioned above), which are attached to the skeleton via a carbonyl group (—CO—);

Alkenyloxycarbonyl: straight-chain or branched alkenyloxy groups having 3 to 10 carbon atoms (as mentioned above) which are attached to the skeleton via a carbonyl group (—CO—);

Alkenylthiocarbonyl: straight-chain or branched alkenylthio groups having 3 to 10 carbon atoms (as mentioned above) which are attached to the skeleton via a carbonyl group (—CO—);

Alkenylaminocarbonyl: straight-chain or branched alkenylamino groups having 3 to 10 carbon atoms (as mentioned above) which are attached to the skeleton via a carbonyl group (—CO—);

Alkenylcarbonyloxy: unsaturated, straight-chain or branched hydrocarbon radicals having 2 to 10 carbon atoms and a double bond in any position (as mentioned above), which is [sic] attached to the skeleton via a carbonyloxy group (—CO$_2$—);

Alkynyl: straight-chain or branched hydrocarbon groups having 2 to 4, 6, 8 or 10 carbon atoms and a triple bond in any position, for example $C_2$-$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

Haloalkynyl: unsaturated, straight-chain or branched hydrocarbon radicals having 2 to 10 carbon atoms and a triple bond in any position (as mentioned above), where the hydrogen atoms in these groups may be partly or fully replaced by halogen atoms, in particular by fluorine, chlorine and bromine;

Alkynyloxy: unsaturated, straight-chain or branched hydrocarbon radicals having 3 to 10 carbon atoms and a triple bond in any position which is not adjacent to the hetero atom (as mentioned above), which are attached to the skeleton via an oxygen atom (—O—);

Haloalkynyloxy: unsaturated, straight-chain or branched alkynyloxy groups having 3 to 10 carbon atoms (as mentioned above), where the hydrogen atoms in these groups may be partly or fully replaced by halogen atoms as mentioned above, in particular by fluorine, chlorine and bromine;

Cycloalkyl: monocyclic, saturated hydrocarbon groups having 3 to 6, 8, 10 or 12 carbon ring members, for example $C_3$-$C_8$-cycloalkyl such as cyclopropyl, cyclobutyl, cyclopentyl, cyclohexyl, cycloheptyl and cyclooctyl;

Cycloalkoxy: monocyclic, saturated hydrocarbon groups having 3 to 12 carbon ring members (as mentioned above) which are attached to the skeleton via an oxygen atom (—O—);

Cycloalkylthio: monocyclic, saturated hydrocarbon groups having 3 to 12 carbon ring members (as mentioned above) which are attached to the skeleton via a sulfur atom (—S—);

Cycloalkylamino: monocyclic, saturated hydrocarbon groups having 3 to 12 carbon ring members (as mentioned above) which are attached to the skeleton via an amino group (—NH—);

Cycloalkylcarbonyl: monocyclic, saturated hydrocarbon groups having 3 to 12 carbon ring members (as mentioned above) which are attached to the skeleton via a carbonyl group (—CO—);

Cycloalkoxycarbonyl: a monocyclic cycloalkoxy group having 3 to 12 carbon ring members (as mentioned above) which is attached to the skeleton via a carbonyl group (—CO—);

Cycloalkylthiocarbonyl: a monocyclic cycloalkylthio group having 3 to 12 carbon ring members (as mentioned above) which is attached to the skeleton via a carbonyl group (—CO—);

saturated or partially unsaturated cyclic radical which, in addition to carbon atoms, may contain hetero atoms from the group consisting of oxygen, sulfur or nitrogen as ring members: cycloalkyl having 3 to 12 carbon ring members as mentioned above or 5- or 6-membered heterocycles (heterocyclyl) containing, in addition to carbon ring members, one to three nitrogen atoms and/or one oxygen or sulfur atom or one or two oxygen and/or sulfur atoms, for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3- dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl;

Aryl: a mono- to tricyclic aromatic ring system containing 6 to 14 carbon ring members, for example phenyl, naphthyl and anthracenyl;

Aryloxy: a mono- to tricyclic aromatic ring system (as mentioned above) which is attached to the skeleton via an oxygen atom (—O—);

Arylthio: a mono- to tricyclic aromatic ring system (as mentioned above) which is attached to the skeleton via a sulfur atom (—S—);

Arylamino: a mono- to tricyclic aromatic ring system (as mentioned above) which is attached to the skeleton via an amino group (—NH—);

Arylcarbonyl: a mono- to tricyclic aromatic ring system (as mentioned above) which is attached to the skeleton via a carbonyl group (—CO—);

Aryloxycarbonyl: a mono- to tricyclic aryloxy group (as mentioned above) which is attached to the skeleton via a carbonyl group (—CO—);

Arylthiocarbonyl: a mono- to tricyclic arylthio group (as mentioned above) which is attached to the skeleton via a carbonyl group (—CO—);

Arylaminocarbonyl: a mono- to tricyclic arylamino group (as mentioned above) which is attached to the skeleton via a carbonyl group (—CO—);

Arylcarbonyloxy: a mono- to tricyclic aromatic ring system (as mentioned above) which is attached to the skeleton via a carbonyloxy group (—CO$_2$—);

Arylcarbonylthio: a mono- to tricyclic aromatic ring system (as mentioned above) which is attached to the skeleton via a carbonylthio group (—COS—);

Arylcarbonylamino: a mono- to tricyclic aromatic ring system (as mentioned above) which is attached to the skeleton via a carbonylamino group (—CONH—);

Arylsulfonyl: a mono- to tricyclic aromatic ring system (as mentioned above) which is attached to the skeleton via a sulfonyl group (—SO$_2$—);

Aryloxysulfonyl: a mono- to tricyclic aryloxy group (as mentioned above) which is attached to the skeleton via a sulfonyl group (—SO$_2$—);

aromatic ring system which, in addition to carbon ring members, may contain hetero atoms from the group consisting of oxygen, sulfur and nitrogen: aryl as mentioned above or mono- or bicyclic heteroaryl, for example 5-membered hetaryl containing one to four nitrogen atoms or one to three nitrogen atoms and one sulfur or oxygen atom: 5-membered hetaryl ring groups which, besides carbon atoms, can contain one to four nitrogen atoms or one to three nitrogen atoms and one sulfur or oxygen atom as ring members, for example, 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzo-fuzed 5-membered hetaryl containing one to three nitrogen atoms or one nitrogen atom and one oxygen or sulfur atom: 5-membered hetaryl groups which, besides carbon atoms, can also contain one to four nitrogen atoms or one to three nitrogen atoms and one sulfur or oxygen atom as ring members and in which two adjacent carbon ring members or one nitrogen and an adjacent carbon ring member can be bridged by a buta-1,3-diene-1,4-diyl group;

5-membered hetaryl, bonded via nitrogen and containing one to four nitrogen atoms, or benzo-fuzed 5-membered hetaryl, bonded via nitrogen and containing one to three nitrogen atoms: 5-membered hetaryl groups which, besides carbon atoms, can contain one to four nitrogen atoms, or one to three nitrogen atoms, respectively, as ring members and in which two adjacent carbon ring members or one nitrogen and an adjacent carbon ring member can be bridged by a buta-1,3-diene-1,4-diyl group, these rings being bonded to the skeleton via one of the nitrogen ring members;

6-membered hetaryl containing one to three, or one to four, nitrogen atoms: 6-membered hetaryl ring groups which, besides carbon atoms, can contain one to three, or one to four, nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

As for the remaining substituents, these correspond to the substituents described in WO/15552.

Other suitable fungicidal crop protection active ingredients are:

(+)-cis-1-(4-chlorophenyl)-2-(1H-1,2,4-triazol-1-yl)cycloheptanol, metsulfovax, cyprodinil, methyl (E)-2-{2-[6-(2-cyanophenoxy)pyrimidin-4-yloxy]phenyl}-3-methoxyacrylate and the azole active ingredients N-propyl-N-[2,4,6-trichlorophenoxy)ethyl]imidazole-1-carboxamide (prochloraz), (Z)-2-(1,2,4-triazol-1-ylmethyl)-2-(4-fluorophenyl)-3-(2-chlorophenyl)oxirane (epoxiconazole), 1-butyl-1-(2,4-dichlorophenyl)-2-(1,2,4-triazol-1-yl)ethanol (hexaconazole), 1-[(2-chlorophenyl)methyl]-1-(1,1-dimethyl)-2-(1,2,4-triazol-1-ylethanol), 1-(4-fluorophenyl)-1-(2-fluorophenyl)-2-(1,2,4-triazol-1-yl)-ethanol (flutriafol), (RS)-4-(4-chlorophenyl)-2-phenyl-2-(1H-1,2,4-triazol-1-ylmethyl)-butyronitrile, 1-[(2RS,4RS;2RS,4SR)-4-bromo-2-(2,4-dichlorophenyl)tetrahydrofurfuryl]-1H-1,2,4-triazole [sic], 3-(2,4-dichlorophenyl)-2-(1H-1,2,4-triazol-1-yl) quinazolin-4-(3H)-one, (RS)-2,2-dimethyl-3-(2-chlorobenzyl)-4-(1H-1,2,4-triazol-1-yl)-butan-3-ol, bitertanol, triadimefon, triadimenol, bromuconazole, cyproconazole, dichlobutrazole, difenoconazole, diniconazole, etaconazole, fluquinconazole, imibenconazole, propiconazole, flusilazole, tebuconazole, imazalil, penconazole, tetraconazole, triflumizol, metconazole, fluquinconazole, fenbuconazole, triticonazole.

The fungicidal crop protection active ingredients are preferably from the group consisting of: tridemorph, fenpropimorph, fenpropidine and the azole active ingredients, it being possible for one or more active ingredients amongst the group consisting of tridemorph, fenpropimorph and fenpropidine to be present in the soil-applied CR granules according to the invention.

The following are preferred amongst the azole active ingredients: prochloraz, epoxiconazole, hexaconazole, cyproconazole, difenoconazole, propiconazole, flusilazole, diniconazole, triticonazole and tebuconazole, the use of epoxiconazole being especially advantageous.

Also suitable are valinamide active ingredients, preferably:

$N^1$-[1-(4-chlorophenyl)-1-ethyl]-$N^2$-isopropoxycarbonyl-L-valinamide, $N^1$-[1-(4-methylphenyl)-1-ethyl]-$N^2$-isopropoxycarbonyl-L-valinamide, $N^1$-[1-(4-methoxyphenyl)-1-ethyl]-$N^2$-isopropoxycarbonyl-L valinamide, $N^1$-[1-R-(2-naphthyl)-1-ethyl]-$N^2$-isopropoxycarbonyl-L-valinamide.

Preferred amongst the group of the resistance activators is Bion® (5-methyl[sic]benzo[1,2,3]thiadiazole-7-carbothioate).

The following compounds of formula III are preferably employed from amongst the group of the salicylates:

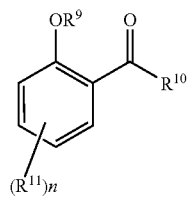

(III)

in which $R^9$ is:

n-, i- or tert-$C_1$-$C_8$-alkyl, $C_1$-$C_8$-alkoxyalkyl or $C_1$-$C_8$-haloalkyl, n- or i-$C_1$-$C_8$-alkylcarbonyl, preferably acetyl, propionyl, benzoyl, $C_1$-$C_8$-alkylbenzoyl, $C_1$-$C_8$-haloalkylbenzoyl, $C_1$-$C_8$-alkoxybenzoyl or hydrogen, hydroxycarbonyl-$C_1$-$C_4$-alkyl, $C_1$-$C_4$-alkoxycarbonyl-$C_1$-$C_4$-alkyl, $R^{10}$ can be hydroxyl, n- or i- or tert-$C_1$-$C_8$-alkyloxy, $C_1$-$C_8$-haloalkyloxy, $C_1$-$C_4$-alkoxy-$C_1$-$C_4$-alkoxy, furthermore amino, $C_1$-$C_8$-alkylcarbonylamino or substituted or unsubstituted arylcarbonylamino or, preferably, benzoylamino, $C_1$-$C_6$-alkylamino, di-$C_1$-$C_6$-alkylamino, substituted (1-3 substituents selected from the group consisting of halogen, CN, $NO_2$, OH, $NH_2$, $CO_2H$, $CONH_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxycarbonyl, $C_1$-$C_4$-alkylamino, di-$C_1$-$C_4$-alkylamino) or unsubstituted arylamino (in particular phenylamino).

$R^{11}$ independently of one another can be:

hydrogen, fluorine, chlorine or iodine, n- or i- or tert-$C_1$-$C_8$-alkyl, $C_1$-$C_8$-alkoxyalkyl or $C_1$-$C_8$-haloalkyl, furthermore an aryl radical of formula IV,

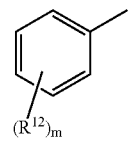

(IV)

which is unsubstituted or mono- or up to trisubstituted and in which the index m or n can be 0-3 and the radical $R^{12}$ has the meaning given for $R^{11}$.

Especially preferred are the compounds:

acetylsalicylic acid, salacetamide, salicylamide, ethenzamide diflunisal, salicylanilide and (2-carbamoylphenoxy) acetic acid.

The crop protection active ingredients may also be in the form of their salts or metal complexes. The invention also extends to the compositions obtained in this manner.

The salts are prepared by reaction with acids, for example hydrohalic acids such as hydrofluoric acid, hydrochloric acid, hydrobromic acid or hydroiodic acid, or sulfuric acid, phosphoric acid, nitric acid or organic acids such as acetic acid, trifluoroacetic acid, trichloroacetic acid, propionic acid, glycolic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid or 1,2-naphthalenedisulfonic acid.

Metal complexes can optionally contain just one or else more than one crop protection active ingredient. It is also possible to prepare metal complexes which contain these active ingredients together in the form of a mixed complex.

Metal complexes are prepared from the organic molecule on which they are based and an inorganic or organic metal salt, for example the halides, nitrates, sulfates, phosphates, acetates, trifluoroacetates, trichloroacetates, propionates, tartrates, sulfonates, salicylates or benzoates of the metals of the second Main Group such as calcium and magnesium and the third and fourth Main Group such as aluminum, tin or lead, and the first to eighth B group such as chromium, manganese, iron, cobalt, nickel, copper and zinc. Preferred are the B group elements of the 4th period, in particular copper. The metals can exist in the various valences which they can assume. The metal complexes can contain one or more organic moieties as ligand.

Control of harmful fungi with the soil-applied CR granules according to the invention is expediently carried out in such a manner that a fungicidally active amount of the soil-applied CR granules is allowed to act in or on the soil, on the seed applied to the soil, or on the plants developing therefrom, or on seedlings.

In the case of annual plants, the soil-applied CR granules according to the invention are preferably applied concomitantly with sowing. Modification of the commercially available seed drills allows the granules to be applied in the same drill coulter together with the seed. Thus, the soil-applied CR granules according to the invention are deposited at the same or different depth as the seed. The number of active-ingredient-comprising granules per seed kernel may vary. The seed drills are equipped with a separate tank for the soil-applied CR granules according to the invention. The bulk of the soil-applied CR granules according to the invention is separated into individual granules via a metering device which is similar to the seed metering device and fed to the common drill coulter via a separate tube. Commercially available drilling systems for seed and granules which have been developed for the concomitant application of fertilizers and seeds may be employed as the seed drills.

The controlled release of the active ingredients allows the release rate of the active ingredients in the soil to be controlled in such a way that, for example in the case of the fungicidal crop protection active ingredients, effective protection against fungal diseases can be maintained over the entire vegetation period. Active ingredient is taken up continuously via the roots to the same extent as the active ingredients are released, from the active ingredients formulated according to the invention, in a controlled fashion, and, via the roots, the active ingredients are then distributed systemically within the plant.

The process according to the invention has the following advantages over spray application of the crop protection active ingredients, which is widely used for controlling fungi:

A single application into the soil, of the active ingredients formulated according to the invention, which preferably takes place concomitantly with the seed or with the planting of seedlings, allows an effective protection of the plant over the entire vegetation period to be achieved, for example against fungal diseases.

This dispenses with the hitherto customary application of several spray applications to the growing crop, thus allowing a considerable saving of labor.

Application of the crop protection active ingredients in the form of the formulation according to the invention may result in smaller amounts of active ingredients to be applied.

A drift of the crop protection active ingredients—as is encountered during spray application—is excluded by this application.

The use of the process according to the invention may dispense with seed dressing.

The soil-applied CR granules according to the invention are preferably produced as coated granules by first applying the active ingredients to solid, granular carriers. The resulting active-ingredient-comprising granules are subsequently coated with suitable coating substances which cause a delayed, controlled release of active ingredient.

Examples of suitable solid carriers for the soil-applied CR granules according to the invention are mineral earths such as silica gel, silicas, silica gels [sic], silicates, talc, kaolin, limestone, lime, chalk, bole, sand, loess, clay, dolomite, diatomaceous earth, calcium sulfate, magnesium sulfate, magnesium oxide, ground synthetic substances, fertilizers such as ammonium sulfate, ammonium phosphate, ammonium nitrate, ureas, for example crotonylidenediurea, isobutylidenediurea, and plant products such as cereal meal, corn meal, tree bark meal, wood meal and nutshell meal, corn grits, cellulose powder, fertilizers. Preferred as carriers are fertilizer granules or fertilizer pellets, in particular those which contain phosphate. Sand is very especially preferred.

In general, the granules have a particle diameter of 0.1 to 10 mm, preferably 0.5 to 8 mm, in particular 0.5 to 3 mm.

As a rule, the active ingredients are applied to the carriers in such a manner that they are sprayed on in the form of oil-in-water emulsions, emulsion concentrates, suspoemulsions, suspension concentrates or as a solution in organic solvents or, preferably, in water.

Spraying takes place, for example, in fluidized-bed coaters or in drums or rotating disks in which the carrier granules are rolled, in perforated vats with controlled drying medium supply, expediently air, or nitrogen. In general, temperatures between 30° C. and 180° C., preferably 35° C. to 90° C., are used for spraying-on and for drying.

The active-ingredient-comprising granules can be manufactured as carrier granules.

In principle, carrier granules are composed of three layers, a core (absorptive or non-absorptive) which is inert to the active ingredients, a layer of one or more active ingredients, and a final coating of a semipermeable film former. Depending on the application, release of the active ingredients can be adjusted in a targeted manner. The active ingredient(s) can be fixed underneath the film former, and the film former acts as the final layer which governs the release rate of active ingredient per unit time. The active ingredient can be applied to the carrier surface together with the film former, this resulting in pores in the film layer which contain active ingredient. In this manner, release of the active ingredient is governed by the proportion of active ingredient in the particular stratum of the coating. A further possibility of constructing granules consists in applying active ingredient and film former in layers, analogously to the structure of an onion. This construction allows release rates which vary over time to be set since the concentration gradient first causes the active ingredients to be released from the outer layers. Thus, a higher active ingredient content in a deeper layer causes a greater release of active ingredient at a later time of the growth stage. Active ingredients on the surface of the granules lead to an initial effect since these active ingredient components are dissolved first and are available for uptake by the plants.

The active ingredients and the film formers are preferably applied in fluidized-bed coaters. The movement in the fluidized bed permanently causes a certain degree of abrasion, which acts as micropores in the film former and thus renders coating polymers, which are, in principle, impermeable, permeable to the active ingredient molecules. As shown in Example 12, the release rate of the active ingredient can be set in a targeted fashion via the heat supplied during the fludized-bed coating process.

The carrier comprising the active ingredient which has been applied is subsequently coated with suitable coating materials. Coating materials which are employed for the controlled release of active ingredient from the coated granules are aqueous polymer dispersions, for example wax dispersions, which comprise—based on the aqueous wax dispersion—5 to 40% by weight of an ethylene copolymer wax consisting of 10 to 25% by weight of an α-olefinically unsaturated mono- or dicarboxylic acid with 3 to 8 C atoms and 90 to 75% by weight of ethylene with an MFI value, measured at 190° C. and a load of 2.16 kp, of from 1 to 600, preferably 5 to 500, in particular 15 to 300, or an MFI value, measured at 160° C. and 325 p, of from 1 to 600, 0.1 to 5% by weight of alkali metal hydroxide, ammonia, an alkanolamine or a dialkanolamine and mixtures of these, and, as remainder, water to 100%.

The ethylene copolymers to be used for the wax dispersion comprise 10 to 25, preferably 15 to 24, % by weight of α-olefinically unsaturated mono- or dicarboxylic acids with 3 to 8 C atoms, amongst which acrylic acid, methacrylic acid, crotonic acid, maleic acid, fumaric acid and itaconic acid may be mentioned by way of example. Preferred amongst these are methacrylic acid and in particular acrylic acid and its mixtures.

The ethylene copolymer waxes are characterized in accordance with the invention by a specific MFI (melt flow index). The MFI indicates the amount of polymer melt in grams which, at a specific temperature, can be squeezed through a nozzle of specific dimensions at a specific expenditure of force (strain). The melt flow indices (MFI units) are determined by standards ASTM D 1238-65 T, ISO R 1133-1696 (E) or DIN 53 735 (1970), all of which are identical with each other.

The wax dispersions furthermore usually comprise bases, namely, as a rule, 0.1 to 5, preferably 1 to 3, % by weight of alkali metal hydroxide, preferably potassium hydroxide or sodium hydroxide, ammonia, a mono-, di- or trialkanolamine having in each case 2 to 18 C-atoms in the hydroxyalkyl radical, preferably 2 to 6 C atoms, or mixtures of the abovementioned alkanolamines or a dialkylmonoalkanolamine having in each case 2 to 8 C atoms in the alkyl and the hydroxyalkyl radicals, or mixtures of these. Examples of amines which may be mentioned are diethanolamine, triethanolamine, 2-amino-2-methylpropan-1-ol or dimethylethanolamine. Ammonia is preferably used.

The base component in the wax dispersions causes at least some of the carboxylic acid groups in the copolymer waxes to be present in the salt form. Preferably, 50 to 90, especially 60 to 85, % of these groups are neutralized.

The coating layer may comprise additional substances for controlling the release of the active ingredients. Examples of these are water-soluble substances such as polyethylene glycols, polyvinylpyrrolidone, polyvinylpyrrolidone/polyvinyl acetate copolymers. For example, they amount to 0.1 to 5% by weight, preferably 0.1 to 3% by weight, based on the coating material.

Coating polymer dispersions which are suitable are combinations of water-insoluble polymers which can be processed as an aqueous or solvent-containing dispersion, such as, for example, copolymer dispersion of acrylic and methacrylic esters, polyethylene wax emulsions (75-90% ethylene, 10-25% α-olefinically unsaturated mono- or dicarboxylic acid), 50 mol % dimethyl terephthalate+approx. 50 mol % adipic acid+150 mol % 1,4-butanediol, 10-95% polyvinyl acetate+5-90% N-vinylpyrrolidone-comprising polymer (Kollidon 30, BASF AG), zinc salt of ethylenemethacrylic acid (see Table 1).

The coating layer is expediently applied by spraying on solutions, dispersions or dispersions [sic] of the abovementioned coating materials in organic solvents or water. An aqueous suspension or an emulsion of the coating material which, in particular, comprises 0.1 to 50, especially 1 to 35, % by weight of polymer material is preferably used. Further auxiliaries for optimizing processability may also be added, for example surfactants, solids such as talc and/or magnesium stearate and/or starch.

TABLE 1 polymer dispersions

| Coating polymer | Composition | Manufacturer |
|---|---|---|
| A | Acronal ® 290D | butyl acrylate/styrene copolymer | BASF AG |
| B | Acronal ® A 603 | copolymer dispersion of acrylic and methacrylic esters | BASF AG |
| C | Acronal ® S 725 | butyl acrylate/styrene copolymer | BASF AG |
| D | Acronal ® S 760 | butyl acrylate/styrene copolymer | BASF AG |
| E | Acronal ® A 627 | copolymer dispersion of acrylic and methacrylic esters | BASF AG |
| F | Poligen ® WE4 | Polyethylene wax emulsion | BASF AG |
| G | Poligen ® WE3 | polyethylene wax emulsion (75-90% ethylene, 10-25% α-olefinically unsaturated mono- or dicarboxylic acid, | BASF AG |
| H | Polyester | 50 mol % dimethyl terephthalate + approx. 50 mol % adipic acid + 150 mol % 1,4-butanediol | BASF AG |
| I | PVA | 10-95% polyvinyl acetate + 5-90% N-vinylpyrrolidone-comprising polymer | BASF AG |
| J | Surlyn ® 9970 | zinc ethylenemethacrylate | Exxon |

Especially preferred is a wax dispersion comprising 5 to 40% by weight of an ethylene copolymer wax, 0.1 to 5% by weight of ammonia and 55 to 94.9% by weight of water, or is composed of these components, the ethylene copolymer wax being made of 75 to 90% by weight of ethylene units and 10 to 25% by weight of units of an α-olefinically unsaturated mono- or dicarboxylic acid having 3 to 8 C atoms.

The coating polymers used in accordance with the invention are generally known or can be obtained by known methods (cf., for example, EP 166 235, EP-A 201 702, U.S. Pat. No. 5,206,279).

Spraying on is carried out, for example, in fluidized-bed apparatuses or in drums or rotating disks in which the carrier granules are rolled, in perforated vats with controlled drying medium supply, or by air-suspension methods. In general, this is done at temperatures between 10° C. and 110° C.

The resulting coated fungicidal compositions can be used as such for the control according to the invention of fungi with controlled release of active ingredient(s).

However, it may also be advantageous externally to apply additional active ingredients to these compositions. The resulting compositions allow further graduation of the controlled release of active ingredient, the active ingredients applied externally to the coating being important for a more directed initial effect. Additionally, it may be advantageous to use a second coating, which provides a further possibility of controlling the delayed release of the active ingredients.

For example, the fungicidal compositions generally comprise between 0.01 and 15, preferably 0.1 to 10, % by weight of crop protection active ingredient.

Depending on the nature of the desired effect, the application rates are between 0.02 and 5 kg, preferably 0.05 and 3 kg, of crop protection active ingredient per ha.

The fungicidal compositions are distinguished by an outstanding activity against a broad spectrum of phytopathogenic fungi, in particular from the classes of the Ascomycetes and Basidiomycetes.

They are especially important for controlling a large number of fungi on a variety of crop plants such as cereals, for example wheat, rye, barley, oats, rice, oilseed rape, sugar beet, maize, soybeans, coffee, sugar cane, ornamentals and vegetables such as cucumbers, beans, potatoes and cucurbits. The fungicides prepared in accordance with the invention are especially advantageously used for controlling fungi on cereals.

The compositions are expediently applied in such a way that the composition is allowed to act in the soil, on the seed applied to the soil, or on plants developing therefrom, or on seedlings. Application of the composition and application of the seed, or the planting of the seedlings, may be carried out in separate operations, it being possible to apply the composition before or after the seed, or after planting seedlings.

It is especially advantageous to apply the formulated crop protection active ingredients concomitantly with the seed, or the planting of the seedlings.

The examples which follow illustrate the invention.

General Method

Preparation of Controlled-Release Granules

The granules were prepared in three different laboratory fluidized-bed plants. One of the three fluidized-bed coaters is the HKC-0.5/5 TJ by Hüttlin. This is a fluidized bed with a product feed tank A of approx. 5 l and a product feed tank B of approx. 0.5 l. The bottom of the fluidized bed is provided with diagonal slits producing a rotating stream of the fluidizing gas. This leads to uniform mixing of the feed material. The large plant has a diameter of 300 mm and a process chamber height of approximately 800 mm. The fluidized bed has three two-substance nozzles embedded in the bottom. In the small plant by Hüttlin, the container has a diameter of 150 mm and is provided with 2 nozzles. Nozzle diameter: 0.8-1.2 mm (depending on the viscosity of the dispersion feed material), spray pressure: 0.5-1.5 bar. Secondary gas stream: 0.3-1.2 bar. The plant can be operated with air or inert gas. The third fluidized-bed coater is made in-house and has a process chamber diameter of 100 mm. The height of the process chamber is approx. 600 mm. The plant is provided with a perforated bottom or alternatively with a bottom provided with diagonal slits. The plant can be operated with one nozzle in the bottom and one nozzle in the process chamber. All fluidized-bed coaters employed (HKC 5 TJ, HKC 05 TJ and the in-house model) can be operated at axial gas speeds of up to 1.9 m/s and gas temperatures of up to 120° C.

Batches of approx. 200-4000 g were produced for the experiments. First, the plant is charged with the feed granules. For example the following feed granules were tested:

a) water-soluble granules
    Rasenfloranid® (Compo, Münster) fertilizer: diameter 0.7-2 mm, various fractions
    Nitrophos® NP 20/20 (BASF AG, Ludwigshafen) fertilizer: diameter 2-4 mm, various fractions
    prilled urea: prill diameter 0.5-3 mm, various fractions b) insoluble granules
    sand: 0.3-0.8 mm, average size: 0.6 mm
    sand: 0.6-1.2 mm, average size: 0.85 mm
    pumice: approx. 0.4-1 mm
    limestone: approx. 0.6-1.5 mm c) biodegradeable absorptive granules
    paper pulp granules: diameter 0.3-0.9 mm
    corn grit: diameter approx. 1.5-3 mm
    corn straw (corn-cob): diameter 0.5-1.25 mm, various fractions The granules are fluidized using the fluidizing gas and is heated to approx. 35-40° C. Then, a suspension or solution which may comprise 1-6 active ingredients is sprayed on.

Spraying on can be done in 3 ways:

1. Active ingredients are sprayed onto the carrier as the first layer, followed by the polymer layer. If appropriate, active ingredient formulations which are not miscible with each other can be sprayed from each of the three nozzles.
2. Active ingredients are mixed with some of the film former, or some of the film former is sprayed within the first 25-50% of the layer with active ingredients from different nozzles, but simultaneously.
3. Active ingredients are sprayed simultaneously with the film former from separate nozzles during the entire coating process from separate nozzles.

During the spraying process, the amount of gas is set to such a level that the granules are agitated thoroughly.

The following compounds were employed in the examples:

Compound 1: Fenpropimorph
(±)-cis-4-[3-(4-tert-butylphenyl)-2-methylpropyl]-2,6-dimethyl-morpholine Compound 2:
1-(4-chlorophenyl)-3-(2-(methoxymethoxycarbonylamino)benzyl)-imidazole Compound 3:
2-[2-(2-isopropoxy-2-(Z)-methoxyimino-1-methyl-(E)-ethylidene-aminooxymethyl)phenyl]-2-(E)-methoxyimino-N-methylacetamide Compound 4:
(E)-2-methoxyimino-2-{2-[(2,5-dimethylphenyl)oxymethyl]phenyl}-N-methylacetamide Compound 5: Bion
5-methyl[sic]benzo[1,2,3]thiadiazole-7-carbothioate Compound 6: epoxiconazole
(2RS,3SR)-1-[3-(2-chlorophenyl)-2,3-epoxy-2-(4-fluorophenyl)-propyl]-1H-1,2,4-triazole Compound 7: acetylsalicylic acid Compound 8: Juwel® (kresoxim-methyl and epoxiconazole)
(Methyl methoxyimino-α-(o-tolyloxy)-o-tolylacetate and (2RS,3SR)-1-[3-(2-chlorophenyl)-2,3-epoxy-2-(4-fluorophenyl)-propyl]-1H-1,2,4-triazole)

Compound 9: Opus® Top epoxiconazole and fenpropimorph

Granule Elution Apparatus

The plant serves to determine the delayed release of active ingredients or salts from controlled release (CR) formulations. A frit on which the granules to be tested are placed is located in a cylindrical vessel at the lower edge. Underneath the frit there is an S-shaped drain which causes liquid to drain from the cylinder only when it is 80% full. Water (if appropriate together with wetter) is pumped through the CR formulations in a cylindrical feed container (approx. volume 100 ml) by means of a hose pump in such a way that the feed material is surrounded completely by water. The percolating water is collected in receiving vessels. An automatic switch causes the receiving vessels to be changed in order to determine the release of active ingredients over time. The receiving vessels are located in a heated water bath so that elution generally proceeds under comparable conditions. Unless elution temperatures are specified, a bath temperature of 30° C. was set.

The elution plant operates 24 hours a day in conjunction with the program control. One elution takes 24 hours, and during this time approx. 4000 ml of fluid are pumped through the feed material and collected in receiving vessels. The active ingredient content in the eluate is determined by means of HPLC or GC. Whether release is uniform can be checked with reference to the feed material. The cumulative value provides a measure for assessing granule permeability.

EXAMPLE 1

Comparison Example

Samples prepared in accordance with EP-A 0 734 204 resulted in plant damage for phytotoxic active ingredients such as, for example, Compounds 1, 6 and 5. Most of the above-mentioned substances result in damage when used at high concentrations, which is also confirmed by the seed-dressing experiments with Compounds 6 and 3 which are shown in Table 2. CR (controlled-release) granules in accordance with formulation 1-5 allow a markedly higher concentration to be fed to the plant over a prolonged period, see Compound 6: 125 g/ha instead of 4 g/ha. However, plant damage is observed even in the case of samples which have been prepared in accordance with EP-A 0 734 204

Preparation: see Example 2, page 29.

The samples were coated with coating material G as described in the process of EP-A 0 734 204.

Emergence failure: 100% loss means no growth after sowing.

Run-out [sic] delay: 100% run-out [sic] delay means no growth after sowing.

The results demonstrate clearly that all formulations result in damage to the treated plant.

EXAMPLE 2

Comparison Example

Table 3 shows yield and disease scores of product samples which had been prepared and tested on spring wheat in accordance with the description which follows.

a) The active ingredient epoxiconazole was processed in the form of a suspension concentrate of the following composition:

| | |
|---|---|
| 500 g/l | of epoxiconazole, |
| 30 g/l | of a block polymer with polypropylene oxide core of approx. molecular weight 3250 onto which ethylene oxide is grafted up to a molecular weight of approx. 6500, as dispersant (BASF, Germany), |
| 20 g/l | of a sodium salt of a condensate of phenolsulfonic acid, urea and formaldehyde, as dispersant (BASF, Germany), and |
| water to 1 l. | The liquid epoxiconazole preparations used in the examples which follow were obtained by diluting this suspension concentrate with a suitable amount of water. | b) The active ingredient fenpropimorph was processed as an oil-in-water emulsion of the following composition:

| | |
|---|---|
| 200 g/l | of fenpropimorph, |
| 37 g/l | of a p-isononylphenol etherified with 8 ethylene oxide units, as emulsifier (BASF, Germany), |
| 87.5 g/l | of a 1:1 mixture (by weight) of 2-ethylhexanoic acid and a p-isononylphenol etherified with 7 ethylene oxide units, as emulsifier (BASF, Germany), and |
| water to 1 l. | |

TABLE 2

Comparison example

| Formulation CR granules No. | Diameter of carrier. [mm] | Amount [g/ha] | [g/ha] | Amount in kg/ha | Coating | Percentage [%] | Thickness of layer [μm] | AI-eluate in % 4000 ml/d AI 1 | AI 2 | Emergence failure [% loss] | Damage [%] | Delayed emergence [%] |
|---|---|---|---|---|---|---|---|---|---|---|---|---|
| 1 | 1.19 | 375 Comp. 1 | 125 Comp. 6 | 17 | G | 5.0 | 13.6 | 61 | 24 | 86 | 56 | |
| 2 | 1.05 | 375 Comp. 1 | 125 Comp. 6 | 23 | G | 7.5 | 18.0 | 18 | 7 | 39 | 19 | |
| 3 | 0.75 | 375 Comp. 1 | 125 Comp. 6 | 18 | G | 3 | 5.1 | 63 | 44 | 90 | 75 | |
| 4 | 0.75 | 375 Comp. 1 | 125 Comp. 6 | 20 | G | 6 | 10.3 | 19 | 6 | 98 | 80 | |
| 5 | 3.05 | 30 Comp. 5 | | 140 | G | 2.0 | 18.4 | 21 | — | 11-25 | 10-28 | |
| Seed-dressing experiment | — | 4 Comp. 6 | — | — | — | — | — | — | — | 100 | 100 | 100 |
| Seed-dressing experiment | — | 50 Comp. 3 | — | — | — | — | — | — | — | 12-25 | 6-15 | 32-70 |

Target crops: spring barley (Beate), spring wheat (Star, Achill)

Preparation: 3000 g of Rasenfloranid were introduced into the fluidized bed as the carrier. The granules were pre-warmed to approx. 35-36° C. by a gas stream of 250-280 m³/h which had been heated to 50° C. The active ingredient suspension (450 g) was sprayed onto the carrier via 3 nozzles at a rate of 24 g/min. The pressure in the two-substance nozzle was 0.8 bar, and a secondary gas stream was applied to aid atomization, also at 0.8 bar. After the active ingredients had been sprayed on, the coating polymer was applied at a spray rate of 25-30 g/min. When spraying the polymer, the inlet air temperature of the gas stream (280 m³/h) was reduced to 40° C., and the product temperature which was established was 28° C. The polymer was processed as an aqueous dispersion with a solids content of 25%.

Markedly less disease and an increase in relative yield was observed in the areas treated with the CR granules in comparison with the untreated plot. The initial release rate of the active ingredients in sample 3 was high, which resulted in phytotoxic damage upon plant emergence. Due to the rapid release of active ingredient, the long-term action of this sample was insufficient, so that only a minor effect was discernible in comparison with the untreated sample.

TABLE 3

Experiments on spring wheat Star

| Formulation | Carrier | Active ingredient | Application rate [g/ha] | Percentage coating | *Erysiphe graminis* Disease level in % | *Leptosphaeria* Disease level in % | relative yield | Yield in dt/ha |
|---|---|---|---|---|---|---|---|---|
| | | Untreated | 0 | | 16 | 25 | 100 | 62 |
| 1 | Rasenfloranid | Comp. 1<br>Comp. 6 | 375<br>125 | 6% | 9 | 18 | 104 | |
| 2 | Rasenfloranid | Comp. 1<br>Comp. 6 | 375<br>125 | 6% | 9 | 18 | 103 | |
| 3 | Rasenfloranid | Comp. 1<br>Comp. 6 | 375<br>125 | 3% | 10 | 22 | 97 | |
| 4 | Rasenfloranid | Comp. 1<br>Comp. 6 | 375<br>125 | 4% | 9 | 17 | 105 | |
| | 2 spray applications, Comp. 10 | | 1000 | | 6 | 9 | 112 | |

EXAMPLE 3

In a stirred vessel, 200 g of vinyl acetate were emulsified in 800 ml of water. The dispersion was treated with a PVP solution (K 30, 20 g solids). In a Hüttlin Kugel Coater (HKC 5) the coating dispersion was applied to carrier granules.

The carrier granules employed were 4000 g of fertilizer pellets of average diameter 1.25 mm. The carrier granules were pre-warmed in the HKC 5 to a product temperature of 40° C., and a mixture of a 20% fenpropimorph emulsion (36.7 g of active ingredient) and a 45% epoxiconazole suspension (5.7 g of active ingredient) was then sprayed onto the granules.

The polymer dispersion was applied as a coating to the carrier granules coated with the active ingredients epoxiconazole and fenpropimorph.

The coating process was carried out under the following conditions:

TABLE 4

| | |
|---|---|
| 3 nozzles (three substance nozzles) | 0.8 mm |
| Weight of carrier granules | 4000 g |
| Air | 400 $m^3$/h |
| Inlet air temperature | 50° C. |
| Product temperature | 40-42° C. |
| Outlet air temperature | 37.5-40° C. |
| Type of spraying operation | continuously |
| Spray pressure | 1 bar |
| Spray rate (for active ingredients and coating polymer) | 12 g/min |
| Process time | 90 min |
| Final drying time to product temperature 50° C. | 15 min |

This gives a uniform smooth coating.

The release rate of the active ingredients was determined in the above-described elution apparatus. To this end, 30 g of the carrier granules were weighed into a trapped container equipped with a frit. In 24 hours, an amount of 3980 g of water was pumped through the container and collected. 124 mg of fenpropimorph and 19 mg of epoxiconazole were detected in the collected liquid.

This product was applied together with cereal seed (winter wheat). On average, approx. 3 fungicidal active ingredient pellets were deposited subterraneously per seed kernel. Epoxiconazole was detected in the growing cereal plants two and six months after application. Two months after sowing, 0.038 mg were detected per kg of biomass, and six months after application 0.022 mg were still detected per kg of biomass.

This demonstrated that the PVA+PVP coating guaranteed a controlled release of the active ingredient epoxiconazole in the soil over at least 6 months.

EXAMPLE 4

The active ingredient granules prepared in accordance with the invention are described by way of example in the tables which follow. In Table 5, column 2 indicates the granule carrier, column 3 the mean diameter of the carrier granules in mm. Columns 4-6 contain the active ingredients and their application rate in g/ha, the columns which follow indicate the active ingredient concentrations in the finished granules (according to HPLC/GC analyses). The amount in kg/ha indicates the total amount of granules required to apply the desired amounts of active ingredient per ha.

The active ingredients were prepared as described in Example 2. The operating conditions of the fluidized-bed plant are described in Table 5+6.

Then, the release of active ingredient in the eluate at 30° C. is indicated in %. The columns which follow indicate the operating conditions for spraying the active ingredient and spraying the coating. Polymer composition, see description pages 22 and 23, active ingredient composition page 27. Some samples were after-baked to improve film formation of the coating polymer at the end of the process.

TABLE 5

| Formulation | Carrier | Carrier diameter [mm] | Rate of active ingredient [g/ha] | | | Active ingredients [actual] | | | Amount |
|---|---|---|---|---|---|---|---|---|---|
| | | | AI1 | AI2 | AI3 | AI1 % | AI2 % | AI3 % | kg/ha |
| 1 | XAF | 1.1 | 375 g/ha Comp. 1 | 125 g/ha Comp. 6 | — | 1.96 | 0.69 | — | 19 |
| 2 | XAF | 1.1 | 375 g/ha Comp. 1 | 125 g/ha Comp. 6 | — | 1.97 | 0.65 | — | 19 |
| 3 | XAF | 1.1 | 375 g/ha Comp. 1 | 125 g/ha Comp. 6 | — | 2.09 | 0.78 | — | 17 |
| 4 | XAF | 1.1 | 375 g/ha Comp. 1 | 125 g/ha Comp. 6 | — | 1.97 | 0.65 | — | 19 |
| 5 | XBF | 3.2 | 250 g/ha Comp. 2 | — | — | 0.17 | — | — | 150 |
| 6 | XBF | 3.2 | 250 g/ha Comp. 3 | — | — | 0.17 | — | — | 146 |
| 7 | XBF | 3.2 | 250 g/ha Comp. 3 | — | — | 0.36 | — | — | 69 |
| 8 | XBF | 3.2 | 250 g/ha Comp. 4 | — | — | 0.19 | — | — | 135 |
| 9 | XBF | 3.2 | 250 g/ha Comp. 4 | — | — | 0.21 | — | — | 117 |
| 10 | XBF | 3.2 | 30 g/ha Comp. 5 | — | — | 0.04 | — | — | 122 |
| 11 | XBF | 3.2 | 30 g/ha Comp. 5 | — | — | 0.03 | — | — | 167 |
| 12 | XBF | 3.2 | 250 g/ha Comp. 3 | — | 30 g/ha Comp. 5 | 0.15 | — | 0.04 | 185 |
| 13 | XAF | 1.3 | — | 125 g/ha Comp. 6 | — | 0.00 | 0.44 | — | 43 |
| 14 | XAF | 1.3 | 30 g/ha Comp. 5 | — | — | 0.11 | — | — | 47 |
| 15 | XKF | 1.4 | 30 g/ha Comp. 5 | 250 g/ha Comp. 3 | — | 0.14 | 0.48 | — | 44 |
| 16 | XKF | 1.4 | 250 g/ha Comp. 3 | 125 g/ha Comp. 6 | — | 0.62 | 0.43 | — | 42 |
| 17 | XKF | 1.4 | 250 g/ha Comp. 3 | 125 g/ha Comp. 6 | 125 g/ha Comp. 7 | 0.58 | 0.36 | 0.30 | 48 |
| 18 | XNF | 0.9 | 200 g/ha Comp. 3 | 125 g/ha Comp. 6 | 30 g/ha Comp. 5 | 1.85 | 1.02 | 0.25 | 12 |
| 19 | XNF | 0.9 | 200 g/ha Comp. 3 | 125 g/ha Comp. 6 | 30 g/ha Comp. 5 | 1.35 | 0.8 | 0.2 | 10 |

XAF Rasenfloranid ®
XBF Nitrophos ® NP 20/20
XKF Urea
XOF Limestone
XNF Sand

Table 6 contains the same granules as Table 5. First, the coating is described in greater detail (type, % and thickness).

TABLE 6

| | | Layer | | | | | | Operating conditions | | | | | | |
|---|---|---|---|---|---|---|---|---|---|---|---|---|---|---|
| | | | | Thickness [μm] calculated | AI eluate, at 4000 ml/24 h | | | Active ingredient | | | Coating | | | |
| Formulation No. | Carrier | Coating polymer | Percentage [%] | | AI1 [%] | AI2 [%] | AI3 [%] | T prod [° C.] | Spray rate [g/min] | Gas [g/min] | T coating prod [° C.] | t coating [min] | Spray rate [g/min] | Gas [m³/h] | After baking [min] |
| 1 | XAF | G | 5.4 | 13 | 53.4 | 23.2 | | 40 | 20 | 268 | 30 | | 30 | 357 | 0 |
| 2 | XAF | I | 5.4 | 13 | 19.1 | 8.8 | | 37 | 26 | 345 | 35 | | 21 | 404 | 0 |
| 3 | XAF | G | 3 | 7 | 18.0 | 7.4 | | 36 | 25 | 340 | 35 | | 20 | 380 | 0 |
| 4 | XAF | G | 4 | 10 | 19.1 | 8.8 | | 37 | 21 | 345 | 34 | | 25 | 370 | 0 |
| 5 | XBF | G | 2 | 18 | 20.9 | | | 40 | 6 | 335 | 38 | 15 | 16 | 345 | 15 |
| 6 | XBF | G | 2 | 18 | 76.6 | | | 40 | 12 | 335 | 38 | 12 | 20 | 335 | 15 |
| 7 | XBF | G | 4 | 37 | 22.2 | | | 40 | 25 | 375 | 38 | 10 | 24 | 395 | 15 |
| 8 | XBF | G | 2 | 18 | 2.6 | | | 40 | 25 | 375 | 38 | 10 | 20 | 395 | 15 |

TABLE 6-continued

| | Layer | | | | | | | Operating conditions | | | | | | |
|---|---|---|---|---|---|---|---|---|---|---|---|---|---|---|
| | | | Thick- | | | | Active ingredient | | | Coating | | | | |
| Formulation No. | Coating Carrier | Per- cent- age poly- mer [%] | ness [μm] calcu- lated | AI eluate, at 4000 ml/24 h | | | T prod [°C.] | Spray rate [g/min] | Gas [g/min] | T prod [°C.] | t coat- ing [g/min] | Spray rate [g/min] | Gas [m³/h] | After baking [min] |
| | | | | AI1 [%] | AI2 [%] | AI3 [%] | | | | | | | | |
| 9 | XBF | G | 4 | 37 | 0.3 | | | 40 | 8 | 350 | 38 | 25 | 19 | 370 | 15 |
| 10 | XBF | G | 2 | 18 | 47.6 | | | 39 | 25 | 360 | 40 | 13 | 19 | 380 | 15 |
| 11 | XBF | G | 4 | 37 | 12.7 | | | 40 | 25 | 370 | 38 | 21 | 23 | 390 | 15 |
| 12 | XBF | G | 4 | 37 | 56.4 | | 20.0 | 40 | 9 | 400 | 46 | 12 | 20 | 370 | 15 |
| 13 | XBF | G | 6 | 18 | | 6.1 | | 33 | 6 | 440 | 43 | 23 | 42 | 470 | 30 |
| 14 | XBF | G | 6 | 18 | 24.3 | | 32 | 25 | 300 | 39 | 46 | 21 | 360 | 30 | |
| 15 | XBF | G | 6 | 18 | 0.0 | 0.0 | | 30 | 25 | 340 | 42 | 34 | 28 | 340 | 30 |
| 16 | XKF | G | 6 | 18 | 78.9 | 8.2 | | 38 | 25 | 330 | 44 | 35 | 27 | 380 | 30 |
| 17 | XKF | G | 6 | 18 | 51.4 | 15.1 | 61.1 | 43 | 12 | 330 | 46 | 36 | 27 | 420 | 30 |
| 18 | XNF | H | 12 | 36 | 7.2 | 1.8 | 9.0 | 36 | 5 | 45 | 38 | 30 | 5 | 50 | 20 |
| 19 | XNF | G | 12 | 36 | 1.3 | 0.7 | 4.3 | 37 | 5 | 42 | 41 | 30 | 5 | 50 | 20 |

The granules were prepared as described for Example 4.

EXAMPLE 5

Table 7 gives a variety of coating polymers which were tested for their suitability for controlled-release granules.

Sample Preparation:
1) Feed 3000 g of carrier material into the fluidized bed, pre-heat to 35° C.
2) Spray on a 40% epoxiconazole suspension which, in addition to active ingredient, also comprises dispersant and wetter.

Spray conditions: Gas throughput 300 m³/h, product temperature approx. 33-36° C., spray rate of the active ingredient suspension 20 ml/min 3) Spray polymer from a dispersion, gas throughput 350-380 m³/h, product temperature 35-40° C., spray rate: 20 ml/min At a gas throughput of 350 m³/h, after-bake the polymer for 15 minutes, product temperature 40° C.

TABLE 7

Comparison of the controlled-release properties of various coating polymers

| Formulation (see Example 4) | Carrier | Carrier diameter [mm] | Active ingredient content [%] epoxiconazole | Coating | Coating composition | Concentration of polymer dispersion | Fluid phase of dispersion | Percentage [%] | Layer thickness [μm] | Eluted active ingredient m² granule surface area, g weight and after elution liquid [mg AI/w/ml] |
|---|---|---|---|---|---|---|---|---|---|---|
| 1 | XBF | 3.05 | 0.90 | Poligen WE 3 | G | 25% | Water | 12.0 | 36.0 | 4.4E−7 |
| 2 | XBF | 3.05 | 1.022 | Polyester | H | 20% | Water | 12.0 | 36.0 | 4.3E−6 |
| 3 | XBF | 3.05 | 0.07 | Acronal 290D | A | 20% | Water | 4.0 | 35.6 | 7.0E−6 |
| 4 | XBF | 3.05 | 0.08 | Surlyn 9970 | J | 2% | boiling THF | 1.0 | 8.9 | 1.4E−5 |
| 5 | XBF | 3.05 | 0.49 | PVA (Collicoat) | I | 10% | Water/20% ethanol | 5.0 | 12.0 | 1.4E−5 |
| 6 | XBF | 3.05 | 0.07 | Acronal S 725 | C | 20% | Water | 4.0 | 35.6 | 1.7E−5 |
| 8 | XBF | 3.05 | 0.08 | Poligen WE4 | F | 20% | Water | 4.0 | 35.6 | 2.2E−5 |
| 9 | XNF | 3.05 | 0.07 | Acronal A 603 | B | 20% | Water | 4.0 | 35.6 | 2.3E−5 |
| 10 | XNF | 0.75 | 0.07 | Arconal S 760 | D | 20% | Water | 4.0 | 35.6 | 3.5E−5 |

TABLE 7-continued

Comparison of the controlled-release properties of various coating polymers

| Formulation (see Example 4) | Carrier | Carrier diameter [mm] | Active ingredient content[%] epoxiconazole | Coating | Coating composition | Concentration of polymer dispersion | Fluid phase of dispersion | Percentage [%] | Layer thickness [μm] | Eluted active ingredient m² granule surface area, g weight and after elution liquid [mg AI/w/ml] |
|---|---|---|---|---|---|---|---|---|---|---|
| 14 | XNF | 0.75 | 0.07 | Arconal A 627 | E | 20% | Water | 4.0 | 35.6 | 6.5E−5 |

XBF NP 20/20
XNF sand

EXAMPLE 6

The CR granules comprise systemic strobilurins as active ingredients, which, surprisingly, do not suffer from the poor efficacy of the azoles and morpholines (of Table 3). In Tables 8 a and b, 2 CR granule samples with a strobilurin of the oxime ether type and a 2 and 4% coating were tested against two spray applications of a strobilurin+azole Juwel®) in winter barley.

For both CR granules (base: Nitrophos® NP 20/20), a duration of action of 8 months and a marked reduction in disease, resulting in a comparable yield as for the spray-treated area, were found. The sample with the thinner coating proved to be less efficient shortly before harvesting, leading to a yield loss of 7% compared with the CR sample with the thicker coating. The fact that comparable biological results can be achieved with a markedly lower rate of active ingredient in comparison with spraying is especially noteworthy.

TABLE 8a

Experiments on winter barley Danilo

| Formulation (see Example 4) | Carrier | Active ingredient Untreated | Application rate [g/ha] | Coating percentage | Rhynchosporium Disease in [%] | Relative yield | Yield dt/ha |
|---|---|---|---|---|---|---|---|
| | | | 0 | | 14 | 100 | 62.4 |
| 6 | NP 20/20 | Comp. 3 | 250 | 2% | 6 | 122 | |
| 7 | NP 20/20 | Comp. 3 | 250 | 4% | 2 | 129 | |
| | | 2 spray treatments with Comp. 8 | 500 | | 0 | 132 | |

TABLE 8b

Experiments on winter barley Noveta

| Formulation (see Example 4) | Carrier | Active ingredient Untreated | Application rate [g/ha] | Coating percentage | Pyrenophora Disease in [%] | Relative yield | Yield dt/ha |
|---|---|---|---|---|---|---|---|
| | | | 0 | | 19 | 100 | 72.5 |
| 6 | NP 20/20 | Comp. 3 | 250 | 2% | 11 | 116 | |
| 7 | NP 20/20 | Comp. 3 | 250 | 4% | 5 | 125 | |
| | | 2 spray treatments with Comp. 8 | 500 | | 0 | 129 | |

EXAMPLE 7

Strobilurin efficacy can be improved even further when several active ingredients are combined with each other, which should be considered to prevent resistance. Tables 9a and b show a comparison of scores and yields achieved with a mixture of various CR granules with the spray treatment. The test material was granules comprising the same strobilurin type as in Tables 8 a and b in combination with granules comprising a systemic resistance inductor (Bion®) together with one more active ingredient.

TABLE 9a

Experiments on winter barley Danilo

| Formulation (see Example 4) | Carrier | Active ingredient Untreated | Application rate [g/ha] | Coating percentage | Rhynchosporium Disease in [%] | Puccinia Disease in [%] | Relative yield | dt/ha |
|---|---|---|---|---|---|---|---|---|
| | | | 0 | | 25 | 3 | 100 | 70.9 |
| 8 | NP 20/20 | Comp. 4 | 250 | 2% | 3 | 1 | 146 | |
| 6 | | Comp. 3 | 250 | | | | | |
| 10 | | Comp. 5 | 30 | | | | | |
| | | 2 spray applications Comp. 8 | 500 | | 0 | 0 | 149 | |

TABLE 9b

Experiments on winter barley Noveta

| Formulation (see Example 4) | Carrier | Active ingredient Untreated | Application rate [g/ha] | Coating percentage | Pyrenophora Disease in [%] | Relative yield | Yield dt/ha |
|---|---|---|---|---|---|---|---|
| | | 0 | | | 22 | 100 | 61.7 |
| 8 | NP 20/20 | Comp. 4 | 250 | 2% | 5 | | 128 |
| 6 | | Comp. 3 | 250 | | | | |
| 10 | | Comp. 5 | 30 | | | | |
| | 2 spray applications | Comp. 8 | 500 | | 1 | | 125 |

EXAMPLE 8

In Table 10, the CR granule formulations of Table 8 are tested in winter wheat. In addition to the CR granules comprising one active ingredient and the mixture of granules comprising various active ingredients (Table 9), this table additionally contains a formulation comprising two active ingredients on one type of granules.

TABLE 10

Experiments on winter barley Frühgold

| Formulation (see Example 4) | Carrier | Active ingredient Untreated | Application rate [g/ha] | Coating percentage | Erysiphe graminis Disease in [%] | Leptosphaeria Disease in [%] | Relative yield | Yield dt/ha |
|---|---|---|---|---|---|---|---|---|
| | | 0 | | | 11 | 63 | 100 | 53.3 |
| 6 | NP 20/20 | Comp. 3 | 250 | 2% | 5 | 40 | | 108 |
| 7 | NP 20/20 | Comp. 3 | 250 | 4% | 4 | 31 | | 120 |
| 12 | NP 20/20 | Comp. 3 | 250 | 4% | 2 | 24 | | 132 |
| | | Comp. 5 | 30 | | | | | |
| | 2 spray applications | Comp. 8 | 500 | | 0 | 2 | | 140 |

In winter wheat, which has a longer growing period, it emerges that the sample with the thicker coating gives better biological results; surprisingly, the sample comprising two active ingredients shows a synergistic effect which exceeds that of the mixture of the individual active ingredient granules of Table 9.

EXAMPLE 9

Again, the synergistic effect in winter wheat is shown clearly in Table 11. In this case, CR granules comprising various active ingredients were mixed (2 or 3 single-ingredient granules).

The product comprising the readymix on one type of granules was much more effective than the granule mixture (see formulations No. 7, No. 9, No. 11 and No. 12, Example 4).

TABLE 11

Experiments on winter wheat Kanzler

| Formulation (see Example 4) | Carrier | Active ingredient Untreated | Application rate [g/ha] | Coating percentage | Erysiphe graminis Disease in % | Leptosphaeria Disease in % | Relative yield | Yield dt/ha |
|---|---|---|---|---|---|---|---|---|
| | | 0 | | | 11 | 32 | 100 | 62.3 |
| 7 | NP 20/20 | Comp. 4 | 250 | 4% | 8 | 18 | | 112 |
| 9 | | Comp. 3 | 250 | | | | | |
| 7 | NP 20/20 | Comp. 4 | 250 | 4% | 3 | 9 | | 114 |
| 9 | | Comp. 3 | 250 | | | | | |
| 11 | | Comp. 5 | 30 | | | | | |
| 12 | NP 20/20 | Comp. 3 | 250 | 4% | 4 | 12 | | 121 |
| | | Comp. 5 | 30 | | | | | |
| | 2 spray applications | Comp. 8 | 500 | | 0 | 3 | | 126 |

EXAMPLE 10

Table 12 shows these super-synergistic effects which are achieved with more than one active ingredient on one type of granules in comparison with granule mixtures, this time on spring wheat. The carriers employed were urea and Rasenfloranid granules.

TABLE 12

Experiments on spring wheat Star

| Formulation (see Example 4) | Carrier | Active ingredient Untreated | Application rate g/ha | Coating percentage | Erysiphe graminis Disease in % | Leptosphaeria Disease in % |
|---|---|---|---|---|---|---|
| | | 0 | | | 9 | 11 |
| 15 | Urea | Comp. 3 | 250 | 6% | 0 | 1 |
| | | Comp. 5 | 30 | | | |
| 16 | Urea | Comp. 3 | 250 | 6% | 1 | 1 |
| | | Comp. 6 | 125 | | | |
| 17 | Urea | Comp. 3 | 250 | 6% | 0 | 1 |
| | | Comp. 6 | 125 | | | |
| | | Comp. 7 | 125 | | | |
| 13 | Rasenfloranid | Comp. 6 | 187 | 6% | 3 | 2 |
| 14 | | Comp. 5 | 30 | | | |
| | 2 spray applications | Comp. 8 | 500 | | 0 | 0 |

Two experimental combinations are noteworthy in this table. Epoxiconazole (Comp. 6.) alone suffered from substantial shortcomings (see Table 3). In combination (granules 2) with the plant activator Bion® (Comp. 5), the effect of epoxiconazole is markedly better. Surprisingly, acetylsalicylic acid (Compound 7) is found to show the same activity-enhancing effects as Bion® (Compound 5) in this experimental series.

EXAMPLE 11

Table 13 shows the effect of a filler in the coating polymer on the release rate. For example, if the cold-water-soluble starch C-Pur® by Ceresta is employed as filler of the coating polymer, the release rate increases markedly with increasing amounts of filler.

TABLE 13

| Active ingredient | Coating percentage | Filler | Release rate in 24 h at 40° C., 4000 ml |
|---|---|---|---|
| Epoxiconazole | 4% | 0% | 2.70% |
| Epoxiconazole | 4% | 10% | 3.30% |
| Epoxiconazole | 4% | 20% | 7.15% |

The granules were prepared by the method described in Example 4.

Batch size: 600 g, inlet air temperature: 45° C., product temperature: 39° C., gas flow rate: 1.8 m/sec

EXAMPLE 12

Table 14 shows how the release rate is affected by the operation of the fluidized-bed drying process. The heat input, in particular, has a marked effect on the leaching properties. The more heat energy is supplied with otherwise constant conditions, the lower the release rate with polymer layers of equal thickness. Doubling of the energy supplied results in a reduction in microporosity of the polymer film to approx. 1/10, which is demonstrated by the release rate.

TABLE 14b

Samples of Table 14a: leaching rate and heat input

| | Leaching rate (% of initial quantity in 4000 ml per 24 h at 30° C.] | | Heat input | Heat input |
|---|---|---|---|---|
| Sample | Comp. 6 | Comp. 3 | [kJ/kg] | [kJ/kg polymer] |
| 1 | 2.1 | 4.9 | 653 | 16,322 |
| 2 | 9.8 | | 517 | 12,927 |
| 3 | 14.9 | | 475 | 11,864 |
| 4 | 19.1 | | 331 | 8282 |
| 5 | 3.2 | 8.02 | 1400 | 15,139 |

The heat input (in kJ/kg) is calculated from the following data:

$Q = \Delta T \cdot V \cdot t \cdot C_p / m$  $Q_{pol} = \Delta T \cdot V \cdot t \cdot C_p / m_{polymer}$ $\Delta T$ = Inlet air temp. minus outlet gas temp. (gas temperature at inlet port minus gas temperature at outlet port)
V = Gas volume flow, calculated from gas flow rate
$C_p$ = Gas constant
t = Total sample residence time (spraying time of the coating polymer+after-baking time)
m = Batch size in kg
$M_{polymer}$ = Amount of polymer in the batch Table 14c—Long-Term Experiment in the Open Granule samples 1 and 5 of Table 14a+b were buried in soil. After 6 months, the samples were analyzed for their residual active ingredient,

| | Leaching rate [% of the originally employed amount after 6 months] | |
|---|---|---|
| Sample | Comp. 6 | Comp. 3 |
| 1 | 12 | 17 |
| 5 | 35 | 45 |

We claim:

1. A process for the preparation of controlled release (CR) granules which contain micropores and are adapted for soil-application, and which are obtained by applying an active-ingredient-comprising coating to a solid carrier in a TABLE 14a

| Sample | Carrier | Active ingredient [%] Comp. 6 | Active ingredient [%] Comp. 3 | % coating Poligen WE3 | Gas flow rate [m/s] | Inlet air temperature [° C.] | Product temperature [° C.] | Outlet gas temperature [° C.] | Spraying time [min] | Spraying rate [g/min] | After-baking time [min] |
|---|---|---|---|---|---|---|---|---|---|---|---|
| 1 | NP 20/20 | 0.091 | 0.16 | 4 | 1.84 | 45.7 | 40.7 | 37.2 | 24 | 26 | 15 |
| 2 | NP 20/20 | 0.076 | | 4 | 1.73 | 45.2 | 40.5 | 37.5 | 24 | 25 | 10 |
| 3 | NP 20/20 | 0.083 | | 4 | 1.53 | 49 | 40 | 38 | 13 | 27.5 | 10 |
| 4 | NP 20/20 | 0.075 | | 4 | 1.61 | 27 | 23 | 23 | 16 | 30 | 20 |
| 5 | urea | 0.394 | 0.80 | 9 | 1.47 | 49.3 | 39.8 | 37.2 | 45 | 24 | 10 |

Fluidized-bed plant, container diameter 300 mm, batchwise operation, batch size: 3-4 kg,
Carrier diameter 3-4 mm, mean layer thickness: 37.5 μm
Samples 1-4: D = 3-4 mm; mean layer thickness approx. 37.5 μm
Sample 5: D = 1.3-2 mm; mean layer thickness approx. 27.5 μm fluidized bed with a defined heat input of from about 11,864 to 25,000 kJ/kg of coating polymer, wherein the CR granules comprise, as coating polymer, a dispersion selected from the group consisting of: butyl acrylate/styrene copolymers, copolymer dispersions of acrylic and methacrylic esters, polyethylene wax emulsions, polyesters composed of the following units: 50 mol % dimethyl terephthalate+approximately 50 mol % adipic acid+150 mol % 1,4-butanediol and ethylene/methacrylic acid zinc salt, which process comprises applying to the carrier in a fluidized bed:

first at least one active ingredient, and then the coating comprising at least one coating polymer and optionally additives, said micropores being generated in the coating by abrasion or by the use of water-soluble additives.

2. The process of claim 1, wherein the lower heat input level is about 12,927 kJ/kg.

3. Controlled release (CR) granules for soil-application, obtained by applying a coating comprising one or more systemically acting strobilurin, as active ingredient, and a coating material selected from the group consisting of: butyl acrylate/styrene copolymers, copolymer dispersion of acrylic and methacrylic esters, polyethylene wax emulsions, polyesters composed of the following units: 50 mol % dimethyl terephthalate+approximately 50 mol % adipic acid+150 mol % 1,4-butanediol and ethylene/methacrylic acid zinc salt to a solid carrier in a fluidized bed with a defined heat input of from about 11,864 to 25,000 kJ/kg of coating material.

4. The CR granules defined in claim 3, wherein the coating comprises:

(a) 0.1-25% by weight of the one or more systemically acting strobilurin, as active ingredient, (b) 1-40% by weight of the coating material, and (c) 0-60% by weight of one or more additives, and wherein the total of the % by weight of the components (a) to (c) amounts to 100% by weight.

5. The CR granules defined in claim 3, comprising, as solid carrier, water-soluble, water-insoluble or biodegradable granules.

6. Soil-applied CR granules as claimed in claim 3, wherein the coating further comprises one or more salicylate, as active ingredient.

7. Soil-applied CR granules as claimed in claim 3, wherein the coating further comprises one or more azole, as active ingredient.

8. Soil-applied CR granules as claimed in claim 6, wherein the coating further comprises one or more azole, as active ingredient.

9. The CR granules defined in claim 3, which wherein the CR granules are obtained by applying the polymer coating to the solid carrier with a heat input of from about 12,927 to 25,000 kJ/kg of coating polymer.

10. Soil-applied CR granules as claimed in claim 3 comprising, as active ingredient, at least one fungicidal compound of the formula I from amongst the class of strobilurins

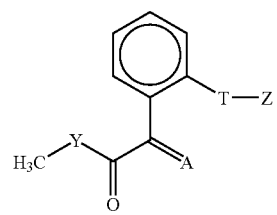

in which the substituents have the following meanings:

A is $NOCH_3$, $CHOCH_3$, $CHCH_3$;

Y is O, NH;

T is oxygen or oxymethylene;

Z is a group X, $N=C(R^1)W$ or $N=C(R^1)—C(R^2)=NOR^3$;

X is unsubstituted or substituted heterocyclyl, unsubstituted or substituted aryl, unsubstituted or substituted hetaryl;

W is unsubstituted or substituted alkyl, unsubstituted or substituted alkenyl, unsubstituted or substituted alkynyl, unsubstituted or substituted cycloalkyl, hetaryl;

$R^1$ is hydrogen, cyano, $C_1$-$C_4$-alkyl, $C_1$-$C_4$-haloakyl, $C_1$-$C_4$-alkoxy, $C_1$-$C_4$-alkoxy-$C_1$-$C_4$-alkoxy-$C_1$-$C_4$-alkyl, $C_3$-$C_6$-cycloalkyl;

$R^2$ is hydrogen, cyano, halogen, $C(R^d)=NOR^3$ or W, OW, SW or $NR^cW$, where $R^c$ is hydrogen, alkyl, alkenyl or alkynyl;

$R^d$ is hydrogen or alkyl;

$R^3$ is hydrogen, unsubstituted or substituted alkyl, unsubstituted or substituted alkenyl or unsubstituted or substituted alkynyl, or a salt thereof.

11. A method for controlling phytopathogenic fungi, undesired vegetation, undesired attack by insects and/or for regulating the growth of plants, which comprises applying the CR granules of claim 3 to the soil which contains or will contain seeds or plants therein.

* * * * *

UNITED STATES PATENT AND TRADEMARK OFFICE
CERTIFICATE OF CORRECTION

PATENT NO. : 7,344,730 B1 Page 1 of 1
APPLICATION NO. : 09/762044
DATED : March 18, 2008
INVENTOR(S) : Stadler et al.

It is certified that error appears in the above-identified patent and that said Letters Patent is hereby corrected as shown below:

In Claim 9, col. 38, indicated line 1:
"which wherein" should read --wherein--

Signed and Sealed this

First Day of July, 2008

JON W. DUDAS
*Director of the United States Patent and Trademark Office*